US009486488B2

(12) United States Patent
Kawasaki et al.

(10) Patent No.: US 9,486,488 B2
(45) Date of Patent: Nov. 8, 2016

(54) SKIN-LIGHTENING AGENT

(75) Inventors: Akiko Kawasaki, Utsunomiya (JP);
Mamiko Kikuchi, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/241,915

(22) PCT Filed: Jul. 18, 2012

(86) PCT No.: PCT/JP2012/068193
§ 371 (c)(1),
(2), (4) Date: Feb. 28, 2014

(87) PCT Pub. No.: WO2013/031403
PCT Pub. Date: Mar. 7, 2013

(65) Prior Publication Data
US 2014/0219940 A1 Aug. 7, 2014

(30) Foreign Application Priority Data

Sep. 1, 2011 (JP) ................................. 2011-190518
Apr. 17, 2012 (JP) ................................. 2012-093771

(51) Int. Cl.
*A61K 36/19* (2006.01)
*A61Q 19/02* (2006.01)
*A61K 8/97* (2006.01)

(52) U.S. Cl.
CPC ................ *A61K 36/19* (2013.01); *A61K 8/97* (2013.01); *A61Q 19/02* (2013.01); *A61K 2800/782* (2013.01)

(58) Field of Classification Search
CPC ..... A61K 36/00; A61K 36/19; A61K 36/195
USPC ................................ 424/725, 779, 763, 778
See application file for complete search history.

(56) References Cited

U.S. PATENT DOCUMENTS

| 2009/0028969 A1 | 1/2009 | Sene et al. |
| 2010/0034757 A1* | 2/2010 | Fujii et al. .................. 424/58 |
| 2011/0033403 A1 | 2/2011 | Lee et al. |

FOREIGN PATENT DOCUMENTS

| JP | 4-211609 A | | 8/1992 |
| JP | 2002-114629 A | | 4/2002 |
| JP | 2002114629 A | * | 4/2002 |
| JP | 2003-089630 A | | 3/2003 |
| JP | 2004-238309 A | | 8/2004 |
| JP | 2005-281206 A | | 10/2005 |
| JP | 2005281206 A | * | 10/2005 |
| JP | 2006-225286 A | | 8/2006 |
| JP | 2009-529499 A | | 8/2009 |
| JP | 2009-298711 A | | 12/2009 |
| JP | 2010-013400 A | | 1/2010 |
| JP | 2010-116371 A | | 5/2010 |
| JP | 2010-159221 A | | 7/2010 |
| JP | 2010-195731 A | | 9/2010 |
| JP | 2010-195732 A | | 9/2010 |
| JP | 2011-37851 A | | 2/2011 |
| JP | 2012-149020 A | | 8/2012 |
| WO | WO 2007/098873 A1 | | 9/2007 |

OTHER PUBLICATIONS

Daniel et al. "Chemosystematics of some Indian members of the Acanthaceae", Proc. Indian Acad Sci (plant Sci), vol. 97, Aug. 1987, pp. 315-323.*
Chondrogianni et al. Anti-aging and rejuvenating effects of quercetin, Experimental Gerontology, 45, (2010), p. 763-771.*
International Search Report (ISR) for PCT/JP2012/068193; I.A. fd: Jul. 18, 2012, mailed Oct. 23, 2012 from the Japanese Patent Office, Tokyo, Japan.
International Preliminary Report on Patentability (IPRP), Chapter I of the Patent Cooperation Treaty, including the Written Opinion for PCT/JP2012/068193; I.A. fd: Jul. 18, 2012, issued Mar. 4, 2014, by the International Bureau of WIPO, Geneva, Switzerland.
Sánchez-Ferrer, A et al., "Tyrosinase: a comprehensive review of its mechanism," Biochim Biophys Acta, Feb. 1995; 1247(1): 1-11, Elsevier Pub. Co., Amsterdam, Netherlands.
Miyachi, Yoshiki et al., Advanced Cosmetic Dermatology, No. 1, Whitening Strategy, Bihaku senryaku, IV: : "Pharmacology and the clinic of the whitening agent," pp. 95-115, 2006, Nankodo Co., Ltd, Tokyo, Japan.
Charoenchai, P et al., "Part 1: Antiplasmodial, cytotoxic, radical scavenging and antioxidant activities of Thai plants in the family Acanthaceae," Planta Med, Nov. 2010; 76(16): 1940-1943, George Thieme, New York, NY.
Arung, ET et al., "Anti-melanogenesis properties of quercetin- and its derivative-rich extract from *Allium cepa*," Food Chemistry, Feb. 2011, 124:1024-1028, Elsevier Applied Science Publishers, Barking, England.
Chinese drug dictionary, vol. 2, (Shangahi Kagaku Gijutsu Shuppansha, Chuyaku Daijiten), 1st edition, third print, "Syaku syou," 1998, pp. 1120-1121, Tetsuo Ouga ed., Shogakukan Co., Ltd, Tokyo, Japan.
Nakanishi, H., "Research and development trend of the recent beautiful own agent. Melanin generation depression effect of the spice" ("Melanin inhibitory activities of perfume"), Chapter 2, Fragrance Journal, 2003, special extra issue No. 18, pp. 113-119, Fureguransujanaru Co. Inc., Japan.
Kubo, I et al., "Flavonols from *Heterotheca inuloides*: tyrosinase inhibitory activity and structural criteria," Bioorg Med Chem, Jul. 2000; 8(7): 1749-1755, Bioorg Med Chem, Oxford, England.
Ko, HH et al., "Antityrosinase and antioxidant effects of ent-kaurane diterpenes from leaves of *Broussonetia papyrifera*," J Nat Prod, Nov. 2008; 71(11): 1930-1933, American Society of Pharmacognosy, Cincinnati, OH.

(Continued)

*Primary Examiner* — Chris R Tate
*Assistant Examiner* — Deborah Davis
(74) *Attorney, Agent, or Firm* — Sterne, Kessler, Goldstein & Fox P.L.L.C.

(57) ABSTRACT

Provided are a very safe skin whitening agent, melanin production inhibitor, and dopa oxidase activity inhibitor. Use of kitsunenomago or an organic solvent extract thereof to inhibit the dopa oxidase activity.

12 Claims, 3 Drawing Sheets

(56) References Cited

OTHER PUBLICATIONS

Chemical Abstracts, AN 2007:889756, 2007, abstract of: Zhang et al., Chemical Study on Rostellularia procumbens, Yingyong Yu Huanjing Shengwu Xuebao (Chinese journal of applied and environmental biology ) (2006) 12(2), 170-175.

FI. China, Wu Zhengyi, editor, vol. 19, Chapter 24: "*Justicia linneaus*, Sp. PI./ 1:15. 1753," pp. 449-461 (2011), Science Press (Beijing) & Missouri Botanical Garden (St. Louis) (China and USA).

Wikipedia entry for: "*Justicia gendarussa*," downloaded from en.wikipedia.org/wiki/Justicia_gendarussa on Aug. 27, 2015.

Abstract of: Takeyama, R. et al., "Quercetin-induced melanogenesis in a reconstituted three-dimensional human epidermal model," J Mol Histol (Feb. 2004), 35(2):157-165, Kluwer Academic Publishers, The Netherlands.

Takeyama, R. et al., " Quercetin-induced melanogenesis in a reconstituted three-dimensional human epidermal model," J Mol Histol. Feb. 2004;35(2):157-165.

Zhang et al., Chemical study on Rostellularia procumbens, (Yingyong Yu Huanjing Shengwu Xuebao), Chinese journal of applied and environmental biology (Apr. 2006) 12(2): 170-175, Science Press of China, Beijing, China.

Chen, Q-X of al., "Kinetics of mushroom tyrosinase inhibition by quercetin," J. Agri. Food Chem (Jul. 2002; available online Jun. 6, 2002), 50:4108-4112, American Chemical Society, Washington, DC.

Chen, L et al., "The activation effect of medicine plants on the mushroom tyrosinase," Journal of Xiamen University (Natural Science), (Dec. 31, 2008), 47:110-114, [Amoy] : Gai da xue publisher, China.

"Acanthaceae," from Wikipedia, printed Mar. 31, 2015, from en/Wikipedia.org/wiki/Acanthaceae (8 pages), page last modified on Feb. 1, 2015.

"*Strobilanthes*," from Wikipedia, printed Mar. 31, 2015, from en/Wikipedia.org/wiki/Strobilanthes (3 pages), page last modified on Apr. 22, 2014.

"*Justicia*," from Wikipedia, printed Mar. 31, 2015, from en/Wikipedia.org/wiki/Justicia (6 pages), page last modified on Feb. 24, 2015.

\* cited by examiner

SKIN-LIGHTENING AGENT

FIELD OF THE INVENTION

The present invention relates to a skin whitening agent, a melanin production inhibitor, or a dopa oxidase activity inhibitor.

BACKGROUND OF THE INVENTION

Cosmetically the white skin with little pigmentation, speckle, or freckle appears to be favored. For this reason a substance having a skin whitening effect and very safe even when used for an extended time is in demand. The pigmentation, spots, freckles, and the like, are generally considered to be caused as a result of the melanin production enhanced by the activated melanocyte present in the skin due to the stimulation from skin exposure to ultraviolet ray, hormonal imbalance, genetic factors, or the like. The mechanism of melanin production enhancement is complicated but it is known that melanin is biosynthesized by the enzyme tyrosinase activity and the dopa oxidase activity of tyrosinase is deeply involved with the melanin production mechanism (Non Patent Document 1). Skin whitening agents targeting this melanin production mechanism have been developed. For example, ascorbic acid, arbutin, kojic acid, and the like, have been reported as skin whitening agents having an effect for inhibiting the melanin production by inhibiting the enzyme tyrosinase activity (Non Patent Document 2).

Plant extracts having a skin whitening effect and inhibiting the dopa oxidase activity have been reported. Examples include toosendan (*Melia toosendan* Sieb. et Zucc.), souka (*Amomum tsao-ka* Crevost et Lemaire), seneshio gurashirisu (*Senecio gracilis*) and kokuriro (*Veratrum nigrum* L.) (Patent Document 1), garden angelica (*Angelica archangelica*), flowering dogwood (*Benthamidia florida*), kansui (*Euphorbia kansui* Liou), Japanese sumac (*Rhus chinensis* Mill.), okazeri (*Cnidium monnieri* (L.) Cuss.), hairvein agrimony (*Agrimonia pilosa* Ledeb.), rouro (*Diuranthera minor* (C. H. Wright) Hemsl.), and common barberry (*Berberis aristata*) (Patent Document 2), inukaramatsu (*Pseudolarix amabilis*), true indigo (*Indigofera tinctoria*) and devil's trumpet (*Datura metel*) (Patent Document 3), pomegranate (*Punica granatum*) flower (Patent Document 4), renshin (a bud of a *Nelumbo nucifera* Gaertn) (Patent Document 5), and *Buddleja axillaris* (Patent Document 6).

Kitsunenomago, *Justicia procumbens*, belonging to the Family Acanthaceae plant is known as shakujo in Kampo and is used for joint pains, fever, or the like. *Justicia gendarussa* (kidachikitsunenomago) also belonging to the same genus plant of the Family Acanthaceae is known as a preparation for external application to the skin analgesic or a preparation for external application to the skin antipruritic (Patent Document 7), and *Thunbergia laurifolia, Rhinacanthus nasuta* (L.) Kurz, and *Andrographis paniculata*, belonging to different genera plants of the same Family Acanthaceae are known to have the tyrosinase activity inhibitory effects, melanin production inhibitory effects, or skin whitening effects (Patent Documents 8 to 10).

However, it has not been known that the Family Acanthaceae, Genus *Justicia*, particularly *Justicia procumbens*, has the melanin production inhibitory effects and skin whitening effects.

CITATION LIST

Patent Document

Patent Document 1: JP-A-2010-195732
Patent Document 2: JP-A-2010-195731
Patent Document 3: JP-A-2010-159221
Patent Document 4: JP-A-2006-225286
Patent Document 5: JP-A-2011-37851
Patent Document 6: JP-A-2009-529499
Patent Document 7: JP-A-2005-281206
Patent Document 8: JP-A-2009-298711
Patent Document 9: JP-A-2003-089630
Patent Document 10: JP-A-2010-013400

Non Patent Document

Non Patent Document 1: Biochimica et Biophysica Acta, 1247, 1-11 (1995)
Non Patent Document 2: Advanced Cosmetic Dermatology, IV. Clinical pharmacology of skin whitening agent ("Bihaku senryaku, IV. Bihakuzaino yakuri to rinsho" in Japanese,) NANKODO Co., Ltd., p. 95-116

SUMMARY OF THE INVENTION

The present invention provides use of kitsunenomago or an organic solvent extract thereof for dopa oxidase activity inhibition.

The present invention also provides use of kitsunenomago or an organic solvent extract thereof for melanin production inhibition.

The present invention also provides use of kitsunenomago or an organic solvent extract thereof for skin whitening.

The present invention further provides use of kitsunenomago or an organic solvent extract thereof for producing an agent of dopa oxidase activity inhibition.

The present invention also provides use of kitsunenomago or an organic solvent extract thereof for producing an agent of melanin production inhibition.

The present invention also provides use of kitsunenomago or an organic solvent extract thereof for producing an agent of skin whitening.

The present invention further provides a method for inhibiting a dopa oxidase activity comprising administration an effective amount of kitsunenomago or an organic solvent extract thereof to the subject.

The present invention also provides a method for inhibiting melanin production comprising administering an effective amount of kitsunenomago or an organic solvent extract thereof to the subject.

The present invention also provides a method for whitening skin comprising administering an effective amount of kitsunenomago or an organic solvent extract thereof to the subject.

DETAILED DESCRIPTION OF THE INVENTION

Figure 1:
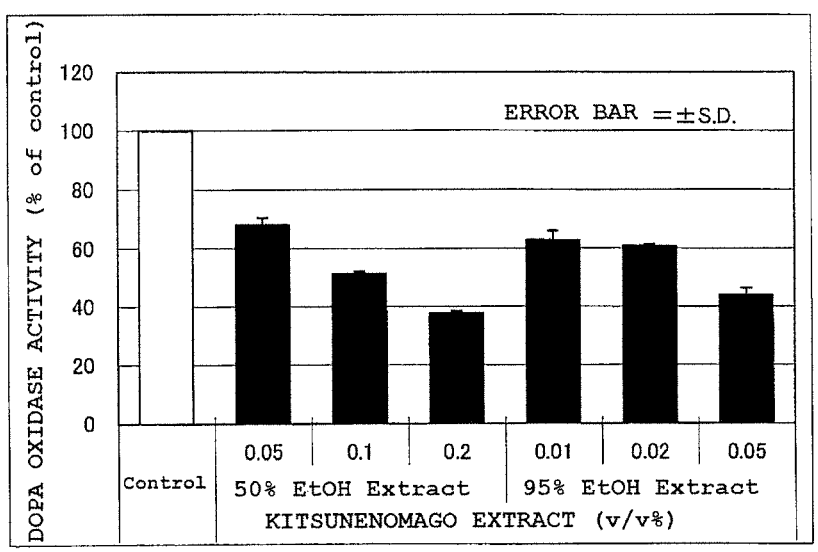
FIG. 1 shows the dopa oxidase activity inhibition by an ethanol extract of kitsunenomago.

The present invention relates to the provision of an agent of skin whitening, an agent of melanin production inhibitor, and an agent of dopa oxidase activity inhibition which are very safe, inhibit the dopa oxidase activity and are useful as a cosmetic product, drug, or the like.

The present inventors searched for a naturally-derived substance having skin whitening effect, melanin production inhibitory effect, or the like, and found that the kitsunenomago belonging to the Family Acanthaceae plant has a dopa oxidase activity inhibitory effect and is useful materials to be a drug, cosmetic product, a preparation for external application to the skin, skin whitening composition, or the like, which are effective in preventing, ameliorating, treating, or the like, the skin browning, spots, freckles, or the like, associated with the melanin overproduction, and accordingly, the present invention has been accomplished.

When the agent of dopa oxidase activity inhibition, the melanin production inhibitor, or the agent of skin whitening of the present invention is used, the melanin overproduction in the skin is inhibited, thereby preventing, ameliorating, or treating skin pigmentation such as suntan, spots, or freckles.

In the present specification, the term "non-therapeutic" refers to the concept which excludes medical practice, that is, treatments to human body by a medical therapy.

In the present invention, the term "amelioration" means to turn a disease, symptoms, or conditions for the better, to prevent or delay a disease, symptoms, or conditions from exacerbating; or to reverse, prevent, or delay a disease, symptoms, or conditions from progressing.

In the present invention, the term "prevention" means to prevent or delay a disease or symptoms in an individual from developing; or to reduce the risk of incidence of a disease or symptoms in an individual.

kitsunenomago in the present invention means *Justicia procumbens* or *Rostellularia procumbens* belonging to the Family Acanthaceae plant.

In the present invention, kitsunenomago is used per se or by cutting, crushing, grinding, squeezing, or drying or powdering the entire plant, leaves (leaf blade, petiole, or the like), fruit (ripe, unripe, or the like), seed, flower (petal, ovary, etc.), stem, rhizome, root, tuberous root, or the like. Preferred part to be used is the entire plant. The extract of kitsunenomago may be any extract from the above parts unless otherwise specified, but the extract from the entire plant is preferred. The extract may be those directly extracted from the plant parts described above, but may also be those extracted after any part of the plant is cut, crushed, ground or squeezed and/or dried or powdered.

The extractant used for preparing a kitsunenomago extract is preferably an organic solvent, and may be a polar organic solvent or nonpolar organic solvent. Examples of the organic solvent include monovalent, bivalent or polyvalent alcohols; ketones such as acetone and methyl ethyl ketone; esters such as methyl acetate and ethyl acetate; linear or cyclic ethers such as tetrahydrofuran and diethyl ether; polyethers such as polyethylene glycol; saturated or unsaturated hydrocarbons; aromatic hydrocarbons such as benzene and toluene; halogenated hydrocarbons such as dichloromethane, chloroform, dichloroethane, and carbon tetrachloride; pyridines; dimethyl sulfoxides; acetonitrile; carbon dioxide, supercritical carbon dioxide; and a fat or oil, waxes, other oils and the like; of these, alcohols and saturated carbon hydrocarbons are preferred in light of pharmacological activities.

The above alcohols are not particularly limited and examples include monovalent alcohols such as methanol, ethanol, propanol, butanol, amyl alcohol, hexanol, heptanol, and octanol; bivalent alcohols such as 1,3-butylene glycol, ethylene glycol, propylene glycol, 1,4-butanediol, 1,5-pentanediol, and 1,6-hexanediol; trivalent or higher alcohols such as glycerol and the like; of these monovalent alcohols and bivalent alcohols are preferred in light of pharmacological activities.

The above alcohols preferably are those having from 1 to 10, more preferably from 1 to 4 carbon atoms. Specific examples include methanol, ethanol, 1,3-butylene glycol, n-propanol, isopropanol, n-butanol, isobutanol, sec-butanol, t-butanol and the like; and ethanol and 1,3-butylene glycol are preferred due to easy managebility.

The saturated hydrocarbons may be linear, branched, or cyclic saturated hydrocarbons, and examples include linear saturated hydrocarbons such as methane, ethane, propane, n-butane, n-pentane, n-hexane, n-heptane, n-octane, n-nonane, and n-decane; branched saturated hydrocarbons such as 2-methylbutane, 2,2-dimethylpropane, 2-methylpentane, 3-methylpentane, 2,2-dimethylbutane, 2,3-dimethylbutane, 2-methylhexane, 3-methylhexane, and 2,2,4-trimethylpentane; cyclic saturated hydrocarbons such as cyclopentane, cyclohexane, and cycloheptane and the like; of these linear saturated hydrocarbons are preferred in light of pharmacological activities.

The above saturated hydrocarbons preferably are those having from 1 to 10, more preferably from 5 to 10, even more preferably from 5 to 8 carbon atoms. Specific examples include n-pentane, n-hexane, n-heptane, n-octane, 2-methylbutane, 2,2-dimethylpropane, 2-methylpentane, 3-methylpentane, 2,2-dimethylbutane, 2,3-dimethylbutane, 2-methylhexane, 3-methylhexane, cyclohexane and the like; and n-hexane is preferred due to easy manageability.

The above organic solvent may be used singly, or two or more may be used as a mixed solvent.

The organic solvent used in the present invention includes an aqueous organic solvent. The aqueous organic solvent is preferably an aqueous hydrophilic organic solvent. The hydrophilic organic solvent is not particularly limited, but examples include a protonic hydrophilic organic solvent such as alcohols, acetic acid, or pyridines, described above, and an aprotic hydrophilic organic solvent such as ketones, acetonitrile, or dimethylsulfoxide; of these, a protonic hydrophilic organic solvent is preferred. The protonic hydrophilic organic solvent is, due to easy manageability preferably the above alcohols, more preferably the above monovalent and bivalent alcohols, even more preferably $C_{1-4}$ alcohols, even more preferably ethanol and 1,3-butylene glycol. These may be used singly, or two or more may be used as a mixed solvent.

The water content in the above aqueous organic solvent is not particularly limited, but may be, in light of pharmacological activities, 70% by volume or less, preferably 50% by volume or less, more preferably 25% by volume or less. For example, it is preferable, in light of pharmacological activities, that the hydrophilic organic solvent concentration in the aqueous organic solvent be 30% by volume or more, more preferably from 50 to 100% by volume, even more preferably from 75 to 100% by volume, even more preferably from 75 to 99.9% by volume.

The extraction technique in the present invention is not particularly limited, and examples include liquid-liquid extraction, solid-liquid extraction, immersion, infusion, decoction, reflux extraction, ultrasonic extraction, microwave extraction, and centrifugal extraction; and they may be used singly or in combinations of two or more. At this time, a batch type extractor, Soxhlet extractor, or the like, may be used.

The extraction conditions are not particularly limited, but the extraction temperature is preferably from 0 to 100° C., more preferably from 4 to 80° C., even more preferably from 4 to 40° C., and the extraction period is preferably from 1 minute to 50 days, more preferably from 1 hour to 50 days, even more preferably from 1 to 30 days. The amount of the solvent used is preferably from 1 to 100 parts by mass, more preferably from 1 to 50 parts by mass, even more preferably from 5 to 40 parts by mass, per part by mass of the plant (on a dried product basis).

The extraction, as an example, is preferably carried out using from 1 to 50 parts by mass of a monovalent or bivalent alcohol aqueous solution (preferably $C_{1-3}$ monovalent alcohols or $C_{3-5}$ bivalent alcohols) comprising 50 to 95% by volume of the above solvent and/or saturated hydrocarbons (preferably $C_{5-10}$ saturated hydrocarbons) per part by mass of a plant (on a dried product basis) at from 10 to 40° C. (preferably from 20 to 40° C.) for from 1 hour to 30 days (preferably from 5 to 20 days). Alternatively, the extraction may be carried out in a nonoxidizing atmosphere while removing the dissolved oxygen by boiling deaeration or passing through an inert gas such as nitrogen gas.

The kitsunenomago extract obtained as described above may be used per se, but may be used as further diluted, concentrated, or freeze-dried, and/or prepared to be a liquid, powder, or paste.

Additionally, after kitsunenomago is extracted with the above solvent, preferably the above hydrophilic organic solvent, an extraction technique such as water washing, liquid-liquid separation, or liquid-solid extraction, may be used because they can remove water-soluble impurities, which is advantageous in light of pharmacological activities. Specifically, a solvent such as water and/or a hydrophobic organic solvent, is added to the kitsunenomago extract, preferably a hydrophilic organic solvent extract, and a physical technique such as mixing, stirring, shaking, or centrifuging is subsequently carried out to recover a fraction (layer) mainly containing pharmacologically active ingredients. This procedure may suitably be repeated 1 to 3 times. After recovery, the fraction may be concentrated and the obtained solid product may be dissolved in an alcohol aqueous solution or the like.

The solvent to be added to the above organic solvent extract (hereinafter referred to as an "additive solvent") may be water, a hydrophobic organic solvent, or a water-hydrophobic organic solvent mixture.

The hydrophobic organic solvent herein is not particularly limited, but examples include saturated or unsaturated hydrocarbons; aromatic hydrocarbons; halogenated hydrocarbons; linear or cyclic ethers or polyethers; oils and the like, as mentioned earlier. Of these, saturated or unsaturated hydrocarbons are preferable in light of pharmacological activities, with saturated hydrocarbons being more preferable. Of the saturated hydrocarbons, $C_{5-10}$ saturated hydrocarbons are preferable, $C_{5-8}$ linear or branched saturated hydrocarbons are more preferable, with n-hexane being even more preferable. These hydrophobic organic solvents may be used singly, or two or more may be mixed and used.

The water-hydrophobic organic solvent mixture when used as the above additive solvent is advantageous because, water washing and the hydrophobic organic solvent extraction can be carried out simultaneously, thereby being efficient in work performance. Water and a hydrophobic organic solvent may be added together or separately to the solvent extract described above. When the extraction, particularly a liquid-liquid separation (distribution), is carrier out using the water-hydrophobic organic solvent mixture, alcohols, inorganic salts, or the like, may further be added for the purpose of improving the layer separation properties or removing acidic ingredients and basic ingredients mixed in the extract. The mixing ratio of water to the hydrophobic organic solvent in the above water-hydrophobic organic solvent mixture is not particularly limited, but is preferably water (v):hydrophobic organic solvent (v)=from 1:0.1 to 1:10, more preferably from 1:0.1 to 1:5.

The above alcohols may be added to the above additive solvent to easily remove the water-soluble impurities, but, in this instance, it is preferable that the content of alcohols in the solvent be from 1 to 50% by volume.

Water-soluble inorganic salts may suitably be added to the above additive solvent to easily remove the water-soluble impurities, and examples of the water-soluble inorganic salt include chlorides such as sodium chloride, and potassium chloride; carbonates such as sodium carbonate; hydrogen carbonates such as sodium hydrogencarbonate; sulfates such as sodium sulfate; phosphates such as sodium phosphate; and the like. The content of water-soluble inorganic salt in water is preferably from 0.5 to 10% (m/v).

The amount of additive solvent to be used is not particularly limited but is preferably from 10 to 100 mL to 1 g of the dried solid product. The extraction temperature is preferably from 4 to 80° C., more preferably from 10 to 40° C., even more preferably from 10 to 30° C.

The organic solvent extract of kitsunenomago obtained as described above may be used per se, but may be used as diluted, concentrated, or freeze-dried, and/or prepared to be a liquid, powder, or paste. Additionally, if necessary, the organic solvent extract of kitsunenomago may be subjected to a separation refining technique such as activated carbon treatment, liquid chromatography, liquid-liquid distribution, gel filtration, or precision distillation, to remove inert impurities and the like, for further refinement.

As described later in Examples, the organic solvent extract of kitsunenomago has outstanding dopa oxidase activity inhibitory effects, which intensely inhibit the dopa oxidase activity. The dopa oxidase activity is deeply associated with the melanin production mechanism (Non Patent Document 1) and for this reason, when the dopa oxidase activity is inhibited, the melanin production inhibitory effects, skin whitening effects, effects for preventing, ameliorating, or treating symptoms of skin pigmentation, spots, and freckles, caused by the skin exposure to ultraviolet rays or the like, can be obtained. In Examples to be described later, the melanin production inhibitory effects rendered by an organic solvent extract of kitsunenomago are also demonstrated.

More specifically, the kitsunenomago or organic solvent extract thereof can be used to inhibit the dopa oxidase activity, inhibit the melanin production, whiten the skin, or prevent, ameliorate, or treat symptoms such as skin pigmentation, spots, or freckles. These uses are applicable to a human or a non-human animal, or tissues, organs, or cells derived therefrom, and may be therapeutic or non-therapeutic.

Accordingly, in an aspect, the present invention provides use of the kitsunenomago or organic solvent extract thereof for dopa oxidase activity inhibition.

The present invention also provides use of the kitsunenomago or organic solvent extract thereof for melanin production inhibition.

The present invention also provides use of the kitsunenomago or organic solvent extract thereof for skin whitening.

Further, the present invention provides the use of kitsunenomago or an organic solvent extract thereof to prevent or ameliorate skin pigmentation, spots, or freckles.

Furthermore, the present invention provides kitsunenomago or an organic solvent extract thereof to be used for preventing or ameliorating skin pigmentation, spots, or freckles.

In one embodiment, the above organic solvent extract can be an alcohol extract.

The above use may be therapeutic or non-therapeutic. In one embodiment, the above non-therapeutic use can be a use for the aesthetic purpose.

In another aspect, the present invention provides an agent of dopa oxidase activity inhibition comprising the kitsunenomago or organic solvent extract thereof as an active ingredient.

The present invention also provides an agent of melanin production inhibition comprising the kitsunenomago or organic solvent extract thereof as an active ingredient.

The present invention also provides an agent of skin whitening comprising the kitsunenomago or organic solvent extract thereof as an active ingredient.

In one embodiment, the above organic solvent extract can be an alcohol extract.

In one embodiment, the above agent may essentially be composed of kitsunenomago or an organic solvent extract thereof.

In another aspect, the present invention provides use of the kitsunenomago or organic solvent extract thereof for producing an agent of dopa oxidase activity inhibition.

The present invention also provides use of the kitsunenomago or organic solvent extract thereof for producing an agent of melanin production inhibition.

The present invention also provides use of the kitsunenomago or organic solvent extract thereof for producing an agent of skin whitening.

The present invention also provides use of kitsunenomago or an organic solvent extract thereof for preventing or ameliorating skin pigmentation, spots, or freckles, or producing a therapeutic agent for the skin.

In one embodiment of the aspect, the melanin production inhibitory effect or the skin whitening effect by the above agent is rendered by the dopa oxidase activity inhibitory effect.

In one embodiment, the above organic solvent extract can be an alcohol extract.

The above kitsunenomago or an extract thereof can be added as a material to compositions, drugs, quasi drugs, preparations for external application, cosmetic products, drink or food products, feeds, or raw materials for drink or food products or feeds for inhibiting the dopa oxidase activity, inhibiting the melanin production, whitening skin, or preventing, ameliorating, or treating symptoms such as skin pigmentation, spots, or freckles; or can be used for producing these products. These compositions, drugs, quasi drugs, preparations for external application, cosmetic products, drink or food products, feeds, and raw materials for drink or food products or feeds, and the like, are also encompassed within the scope of the present invention.

The above compositions, drugs, quasi drugs, preparations for external application, cosmetic products, drink or food products, feeds, or raw materials for drink or food products or feeds can be produced or used for human or non-human animal. The above kitsunenomago or an extract thereof is added to the compositions, drugs, quasi drugs, preparations for external application, cosmetic products, drink or food products, feeds, or raw materials for drink or food products or feeds, and can be the active ingredient for inhibiting the dopa oxidase activity, inhibiting the melanin production, whitening skin, or preventing, ameliorating, or treating symptoms such as skin pigmentation, spots, or freckles.

The drugs or quasi drugs comprise the above kitsunenomago or an extract thereof as the active ingredient. The drugs or quasi drugs can be administered in any administration form. The administration may be oral or parenteral. Examples of the dosage form for oral administration include solid administration forms such as tablets, coated tablets, granules, powders, and capsules, and liquid administration forms such as elixirs, syrups and suspensions; examples of the dosage form for parenteral administration include injections, infusions, topicals, preparations for external application, subcutaneous, transmucosal, transnasal, enteric, inhalation, suppositories, bolus, and patches. The drugs or quasi drugs can be preferably in the form of preparations for external application to the skin.

The cosmetic products comprise the above kitsunenomago or an extract thereof as the active ingredient. Examples of the cosmetic form include any form which can be used for a cosmetic product such as creams, emulsions, lotions, suspensions, gels, powders, packs, sheets, patches, sticks, and cake. The cosmetic products are preferably a skin whitening cosmetic product, and also preferably a cosmetic product for external application to the skin. The cosmetic products are more preferably a cosmetic product for external application for skin whitening.

The drugs, quasi drugs, or cosmetic products may comprise the above kitsunenomago or an extract thereof singly or in combination, or may comprise in combination with a pharmaceutically or cosmetically acceptable carrier. Examples of the carrier include an excipient, coating agent, binder, extender, disintegrator, lubricant, diluent, osmotic pressure regulator, pH regulator, dispersant, emulsifier, preservative, stabilizer, antioxidant, colorant, ultraviolet absorber, moisturizer, thickener, activity enhancer, anti-inflammatory agent, disinfecting agent, perfume, flavor, odor improver and the like. The drugs and quasi drugs may also comprise other active ingredients and pharmacological ingredients insofar as the dopa oxidase activity inhibitory effects of the above kitsunenomago or an extract thereof are not affected. The cosmetic products may also comprise other active ingredients and cosmetic ingredients such as a moisturizer, skin whitening agent, UV protector, cell activator, cleaner, keratolytic agent, and make-up components (e.g., a makeup base, foundation, face finishing powder, powder, cheek color, rouge, eye makeup, eyebrow pencil, mascara, etc.) insofar as the dopa oxidase activity inhibitory effects of the above kitsunenomago or an extract thereof are not affected.

The above drugs, quasi drugs, or cosmetic products can be produced by a routine method from the above kitsunenomago or an extract thereof, or in combination as necessary with the above carrier and/or other active ingredients, cosmetic ingredients, or pharmacological ingredients. For example, the above-described drug or quasi drug for external application to the skin or cosmetic product for external application to the skin can be prepared from the above kitsunenomago or an extract thereof, or in combination with those typically added to preparations for external application, pharmaceutical products for external application, quasi drugs, or cosmetic products for the skin such as oils or oily substances (e.g., fats or oils, waxes, higher fatty acids, essential oils, silicone oils, or the like), moisturizers (e.g., glycerol, sorbitol, gelatin, polyethylene glycol, or the like), powders (e.g., chalks, talcs, Fuller's earth, kaolin, starch, rubber, or the like), dye, emulsifier, solubilizer, cleaner, ultraviolet absorber, thickener, medicinal component, perfume, resin, antibacterial and antifungal agent, other plant extracts (e.g., crude drugs, Kanpo products, herbs), alcohols, polyvalent alcohols, inorganic acids (e.g., bicarbonate, carbonate, sodium chloride, potassium chloride, sodium sulfate, or the like), organic acids (e.g., succinic acid, glutaric acid, fumaric acid, glutamic acid, malic acid, citric acid, ascorbic acid, or the like), vitamins (e.g., vitamin As, vitamin Es, vitamin Bs, vitamin C, folic acid, or the like), water-soluble polymers, anionic surfactants (e.g., alkylbenzene sulfonate, alkylsulfate, or the like), cationic surfactants (e.g., alkyl quaternary ammonium salt, alkyl dimethyl benzyl ammonium salt, or the like), nonionic surfactants (e.g., polyoxyethylene alkyl ether, polyoxyethylene alkyl phenyl ether, or the like), and amphoteric surfactants (e.g., imidazoline or carbobetaine containing an alkyl group, or the like).

In the case of the drug or quasi drug, which is the preparation for external application to the skin, the content of kitsunenomago or an extract thereof in the drug, quasi drug, or cosmetic product is, on a dry weight basis, preferably from 0.00001 to 20% by mass, more preferably from 0.0001 to 10% by mass, and, the content in the cosmetic product is, on a dry weight basis, preferably from 0.0001 to 20% by mass, more preferably from 0.0001 to 10% by mass.

The above drink or food products and feeds are intended to function for inhibiting the dopa oxidase activity, inhibiting the melanin production, whitening skin, or preventing, ameliorating, or treating symptoms such as skin pigmentation, spots, or freckles; and can be drink or food products, functional drink or food products, drink or food products for sick people, drink or foods for specified health uses, pet food, or the like, with the above functions shown thereon as necessary.

The kind of drink or food products described above is not particularly limited. Examples of the drink products include a wide variety of drink products such as fruit juice drinks, carbonated drinks, tea drinks, coffee drinks, milk drinks, alcoholic beverages, and soft drinks. The form of food products may be any form such as solid, semi-solid, or liquid, and may be a tablet form, pill form, tablet, capsule form, liquid form, syrup form, powder form, granule form, or the like. Examples of the food products include breads, noodles, pastas, jellied food products, various snacks, cakes, sweets, ice creams, soups, dairy products, frozen foods, instant food products, other processed food products, seasonings, supplements and the like. The type of the above feed is not particularly limited and may be for any animal, and the form can be any form as in the case of the above food products.

The drink or food products, feeds, or raw materials therefor, may comprise the above kitsunenomago or an extract thereof singly, or may comprise in combination with other food materials or additives such as a solvent, softener, oil, emulsifier, preservative, perfume, stabilizer, colorant, antioxidant, moisturizer, or thickener. The content of the above kitsunenomago or an extract thereof in the drink or food products or feeds is, on a dry weight basis, preferably from 0.0001 to 10% by mass, more preferably from 0.0001 to 5% by mass, even more preferably from 0.001 to 1% by mass.

The present invention provides a method for inhibiting the dopa oxidase activity in cells. The method comprises a step of adding the above kitsunenomago or an extract thereof to a tyrosinase-expressing cell in which the dopa oxidase activity needs to be inhibited.

The present invention provides a method for inhibiting the melanin production in cells. The method comprises a step of adding the above kitsunenomago or an extract thereof to a melanin-producing cell in which the melanin production needs to be inhibited.

In the present invention, the "cell" in which the dopa oxidase activity or melanin production is to be inhibited is not particularly limited, insofar as it is a tyrosinase-expressing or melanin-producing cell that is native or modified by a genetic engineering technique. The cell is preferably pigment cells (melanocyte, retinal pigment epithelial cell, or the like), with melanocyte being more preferable. Alternatively, the "cell" may be a cell debris or cell fraction of the cells mentioned above, tissues containing the cells mentioned above or cultured product derived from the cells mentioned above. When the cell is a cell cultured product, the cell is preferably cultured in the presence of the above kitsunenomago or an extract thereof. The concentration of the above kitsunenomago or an extract thereof to be added is, when the cell is a cell cultured product, as the final concentration in the cultured product, on a dry weight basis, from 0.00001 to 2% (w/v), preferably from 0.00005 to 0.5% (w/v), more preferably from 0.0001 to 0.1% (w/v).

In the present invention, the above kitsunenomago or an extract thereof can be administered or ingested in an effective amount to or by a subject for inhibiting the dopa oxidase activity, inhibiting the melanin production, whitening skin, or preventing, ameliorating, or treating symptoms such as skin pigmentation, spots, or freckles. The administration or ingestion may be carried out nontherapeutically for health promotion or aesthetic purpose. Examples of the subject in the administration or ingestion include animals which need the inhibition of the dopa oxidase activity. Alternatively, examples of the subject in the administration or ingestion include animals who desire the melanin production inhibition or skin whitening, or animals who desire the prevention, amelioration, or treatment of the symptoms such as skin pigmentation, spots, or freckles. The animal is preferably a human or non-human mammal, with a human being more preferable.

The effective amount of administration or ingestion may be an amount which can inhibit the dopa oxidase activity or melanin production of cells in the subject. The preferable amount of administration or ingestion is variable depending on species, body weight, sex, age, conditions of the subject, or other factors. The dose, route, interval of administration or injection, and the amount of ingestion and interval, can be suitably determined by those skilled in the art. For example, when topically administered to the human skin, the amount of administration per adult (60 kg) is preferably from 0.001 to 1 mg/day, more preferably from 0.01 to 0.1 mg/day, on a dry weight basis of kitsunenomago or an extract thereof.

EXAMPLES

The present invention is described below in further detail with reference to Examples, but is not limited thereto.

Production Example

Preparation of a Kitsunenomago Extract

Production Example 1

Preparation of a Kitsunenomago 50% Ethanol Extract 800 mL of 50% ethanol was added to 80 g of kitsunenomago (manufactured by SHINWA BUSSAN CO., LTD.), and a crude extract liquid was obtained by extraction at room temperature for 7 days and filtration. Subsequently, the crude extract liquid was concentrated to dryness to obtain 6.6 g of an extracted solid. The extracted solid was dissolved in 50% ethanol to give an evaporation residue of 1.0 w/v %, thereby preparing a kitsunenomago 50% ethanol extract.

Production Example 2

Preparation of a Kitsunenomago 95% Ethanol Extract 500 mL of 95% ethanol was added to 50 g of kitsunenomago (manufactured by SHINWA BUSSAN CO., LTD.), and a crude extract liquid was obtained by extraction at room temperature for 7 days and filtration. Subsequently, the crude extract was concentrated to dryness to obtain 897 mg of an extracted solid. The extracted solid was dissolved in 95% ethanol to give an evaporation residue of 1.0 w/v %, thereby preparing a kitsunenomago 95% ethanol extract.

Production Example 3

Preparation of a Kitsunenomago 50% Butylene Glycol Extract 100 mL of 50% butylene glycol (BG) was added to 10 g of kitsunenomago (manufactured by Nakanoshima Technos, Co., Ltd.) and extraction was carried out at room temperature for 7 days. Subsequently, the extract was filtered to obtain a kitsunenomago 50% BG extract having an evaporation residue of 1.3 w/v %.

Production Example 4

Preparation of a Kitsunenomago 80% Butylene Glycol Extract 100 mL of 80% BG was added to 10 g of kitsunenomago (manufactured by Nakanoshima Technos, Co., Ltd.) and extraction was carried out at room temperature for 7 days. Subsequently, the extract was filtered to obtain a kitsunenomago 80% BG extract having an evaporation residue of 0.38 w/v %.

Production Example 5

Preparation of a Kitsunenomago 100% Butylene Glycol Extract 100 mL of 100% BG was added to 10 g of kitsunenomago (manufactured by Nakanoshima Technos, Co., Ltd.) and extraction was carried out at room temperature for 7 days. Subsequently, the extract was filtered after 25 mL of water was added thereto to obtain a kitsunenomago 100% BG extract having an evaporation residue of 0.06 w/v %.

Example 1

Dopa Oxidase Activity Inhibition by the Kitsunenomago Extract (1) Cell Culture

Normal human neonatal epidermal melanocytes (NHEMs; KURABO INDUSTRIES, LTD.) were seeded in a 96-well plates at a density of $1 \times 10^4$ cells/well (100 µL/well) and cultured at 37° C. under a 5% $CO_2$. Cells were maintained in Medium 254 (KURABO INDUSTRIES, LTD.) containing growth supplement (HMGS) without PMA.

After 3-day culture, the kitsunenomago extracts prepared in accordance with the above Production Examples 1 to 5 and having an evaporation residue of 1.0 w/v % were each added to give a final concentration shown in Table 1 together with Endothelin-1 (ET-1), SCF, α-MSH, Histamine, and $PGE_2$ adjusted to have a final concentration of 1 nM in each medium, and cultured under the conditions of 37° C. and a 5% $CO_2$ for 3 days. For a control, an ethanol aqueous solution (50% or 95%) or butylene glycol (BG) aqueous solution (50%, 80%, or 100%) of the equal amount was added.

(2) Measurement of Dopa Oxidase Activity

After completion of culture, Alamar Blue (Invitrogen) reagent was added in an amount of 20 µL/well and incubated for 2 to 3 hours, followed by measuring the fluorescence intensity of the medium to measure the cellular respiration activity. Subsequently, the cells were washed with PBS, an extraction buffer (0.1 M Tris-HCL (pH 7.2), 1% NP-40, 0.01% SDS, 100 µM PMSF, 1 µg/m aprotinin) was added in an amount of 20 µL/well, and an assay buffer (4% dimethylformamide, 100 mM sodium phosphate-buffered (pH 7.1)) was added in an amount of 20 µL/well, in which the cells were solubilized at 4° C. for 3 hours, thereby the dopa oxidase activity was measured. The dopa oxidase activity was measured by the following method with reference to the MBTH method (Winder A. et al., 1991, Eur. J. Biochem. 198: 317-326).

To each of the wells containing the solubilized cell solution, 80 µL, of the above assay buffer, 60 µL of 20.7 mM MBTH (3-methyl-2-benzothiazolinon hydrazone) solution, and 40 µL of 5 mM L-dopa(L-dihydroxyphenylalanine) solution as a substrate were added, reacted at 37° C. for 30 to 60 minutes, thereby measuring the color reaction thereof at 490 nm absorbance (N=3). The measured values were shown in the relative value to the result of the control.

(3) Results

Figure 2:
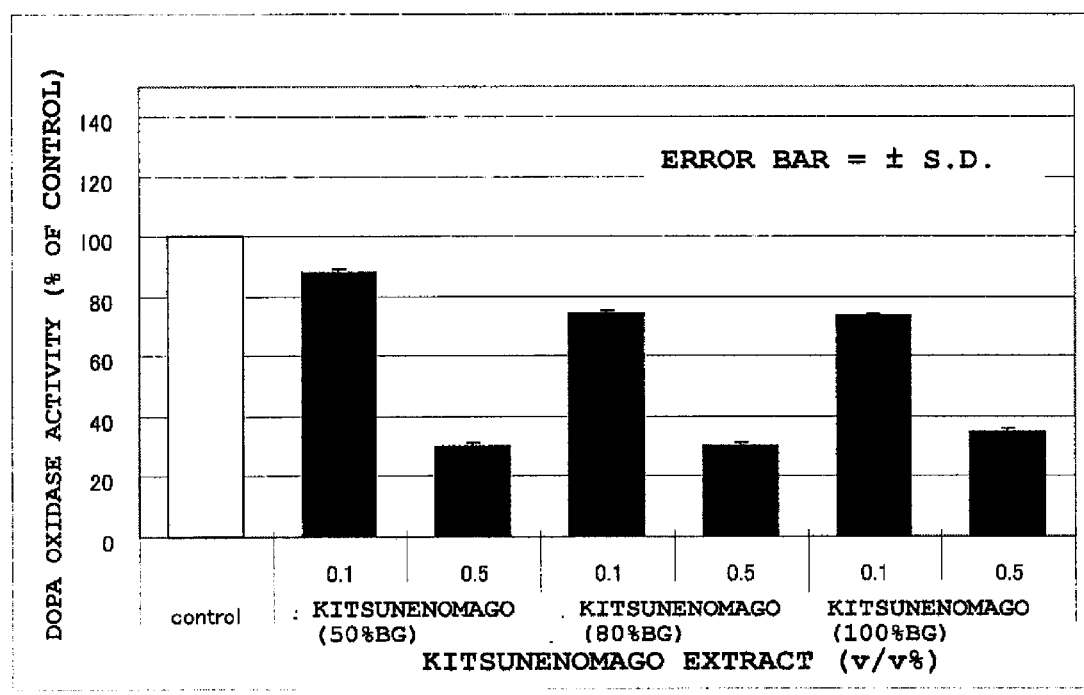
FIG. 2 shows the dopa oxidase activity inhibition by a butylene glycol extract of kitsunenomago.

Table 1 and FIGS. 1 and 2 show the results. The dopa oxidase activity was inhibited by the kitsunenomago 50% ethanol extract, 95% ethanol extract, 50% BG extract, 80% BG extract, and 100% BG extract in an extract addition concentration-dependent manner. The cellular respiration activity measurement by the Alamar Blue method confirmed that the kitsunenomago extract addition at the concentrations shown in Table 1 does not affect the cell growth.

TABLE 1

| Plant | Solvent | Amount added (v/v %) | Extract final concentration (w/v %) | Dopa oxidase activity (%) |
|---|---|---|---|---|
| kitsunenomago | 50% EtOH | 0.05 | 0.0005 | 67.9 |
| | | 0.1 | 0.001 | 51.3 |
| | | 0.2 | 0.002 | 37.7 |
| | 95% EtOH | 0.01 | 0.0001 | 62.8 |
| | | 0.02 | 0.0002 | 60.8 |
| | | 0.05 | 0.0005 | 43.8 |
| | 50% BG | 0.1 | 0.001 | 88.1 |
| | | 0.5 | 0.0065 | 30.1 |
| | 80% BG | 0.1 | 0.00038 | 74.3 |
| | | 0.5 | 0.0019 | 30.1 |
| | 100% BG | 0.1 | 0.00006 | 73.4 |
| | | 0.5 | 0.0003 | 34.7 |

Example 2

Melanin Production Inhibition by a Kitsunenomago Extract

Using EPI-100-NMM113 medium to which ET-1 and SCF were added to give a final concentration of 10 nM, a 3D cultured skin model (MEL300A) was cultured under the conditions of 37° C. and a 5% $CO_2$. On the first day of the culture, the kitsunenomago 50% ethanol extract prepared in accordance with the Production Example 1 and having an evaporation residue of 1.0 w/v % was added to give a final concentration of 0.05 v/v % and 0.1 v/v % (extract final concentration of 0.0005 w/v % and 0.001 w/v %). For a control, a 50% ethanol of the equal amount was added. The medium was exchanged every 3 days. 14 Days later, the cellular respiration activity was measured in the same manner as in Example 1 using the Alamar Blue reagent. Subsequently, the 3D cultured skin was washed with PBS while kept in a cup, which was an incubation substrate, and the skin sheet was then peeled and transferred to a tube using a pair of tweezers, and further washed 3 times with PBS. The skin sheet was washed 3 times with 50% ethanol and twice with 100% ethanol, and allowed to stand at room temperature overnight until completely dried. After finally adding 200 μL of 2M NaOH, the skin sheet was dissolved at 100° C., and the supernatant obtained by centrifugal separation was measured for the absorbance at a measurement wavelength of 405 nm to calculate an amount of melanin. The measured value was shown in the relative value to the result of the control.

Figure 3:
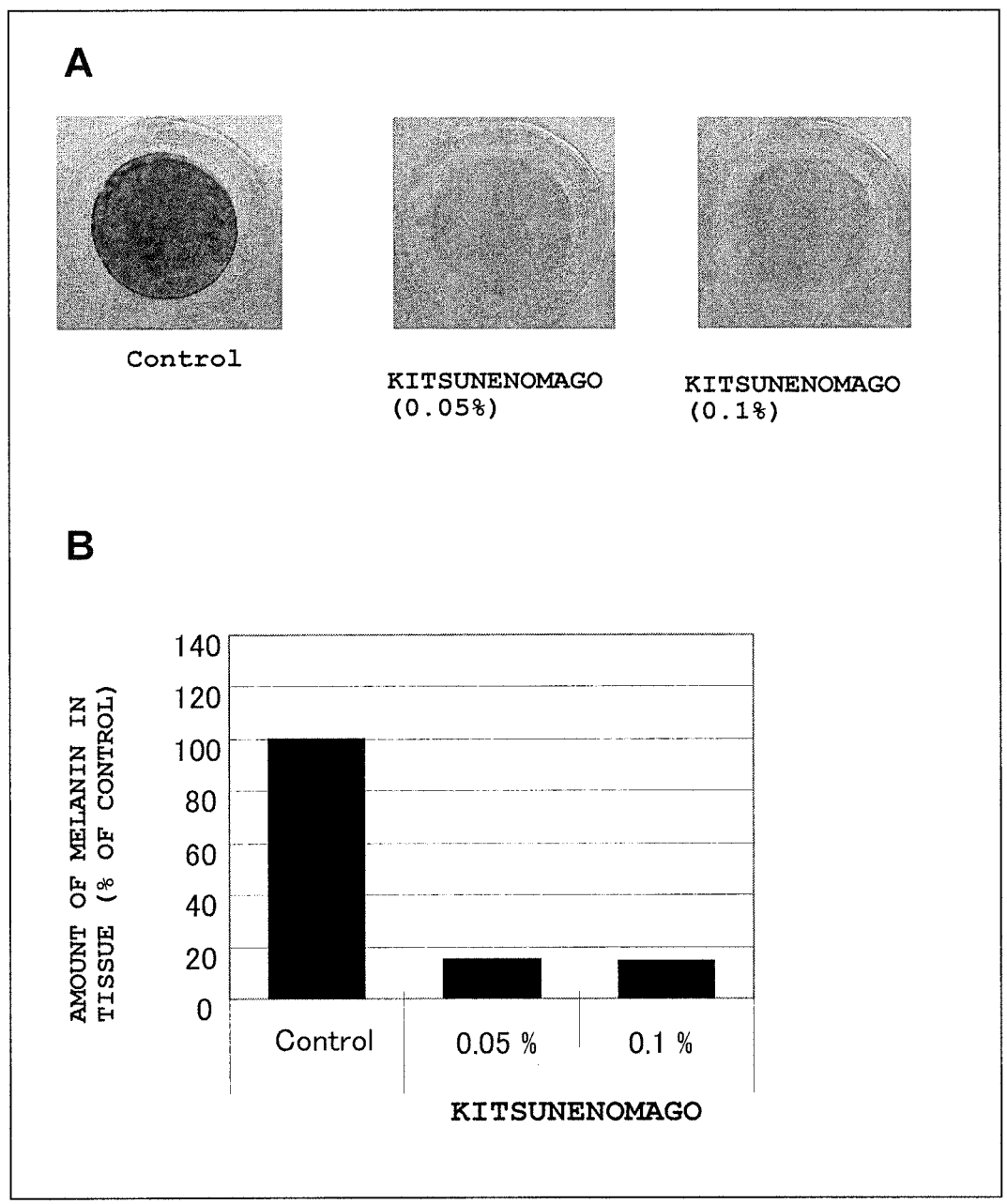
FIG. 3 shows the melanin production inhibition by the kitsunenomago extract.

FIG. 3 shows the photo of 3D cultured skin model on day 14 of the culture and the measurement results of the amount of melanin. The cell darkening inhibitory effect by the kitsunenomago extract addition was visually assured (FIG. 3A), and the amount of melanin in the cells reduced 80% or more (FIG. 3B). Further, the cellular respiration activity measurement by the Alamar Blue method confirmed that the extract at this concentration is not cytotoxic.

What is claimed is:

1. A method for inhibiting dopa oxidase activity in a subject's skin cells, comprising administering to said subject an effective amount of a composition consisting essentially of an organic solvent extract of kitsunenomago, wherein the subject is in need of inhibiting dopa oxidase activity in skin cells.

2. The method according to claim 1, wherein the kitsunenomago organic solvent extract is administered in a preparation for external application or a cosmetic product in which the content of the kitsunenomago organic solvent extract is from 0.0001 to 20% by mass on a dry weight basis.

3. The method of claim 1, wherein the organic solvent extract of kitsunenomago is administered to the subject.

4. The method according to claim 3, wherein the organic solvent extract of kitsunenomago is prepared by extracting kitsunenomago with an organic solvent at a temperature of from 4 to 40° C. for 1 to 30 days.

5. A method for inhibiting melanin production in a subject's skin cells, comprising administering to said subject an effective amount of a composition consisting essentially of an organic solvent extract of kitsunenomago, wherein the subject is in need of inhibiting melanin production in skin cells.

6. The method according to claim 5, wherein the kitsunenomago organic solvent extract is administered in a preparation for external application or a cosmetic product in which the content of the kitsunenomago organic solvent extract is from 0.0001 to 20% by mass on a dry weight basis.

7. The method of claim 5, wherein the organic solvent extract of kitsunenomago is administered to the subject.

8. The method according to claim 7, wherein the organic solvent extract of kitsunenomago is prepared by extracting kitsunenomago with an organic solvent at a temperature of from 4 to 40° C. for 1 to 30 days.

9. A method for whitening a subject's skin cells, comprising administering to said subject an effective amount of a composition consisting essentially of an organic solvent extract of kitsunenomago, wherein the subject is in need of whitening the skin cells.

10. The method according to claim 9, wherein the kitsunenomago organic solvent extract is administered in a preparation for external application or a cosmetic product in which the content of the kitsunenomago organic solvent extract is from 0.0001 to 20% by mass on a dry weight basis.

11. The method of claim 9, wherein the organic solvent extract of kitsunenomago is administered to the subject.

12. The method according to claim 11, wherein the organic solvent extract of kitsunenomago is prepared by extracting kitsunenomago with an organic solvent at a temperature of from 4 to 40° C. for 1 to 30 days.

* * * * *